US006281346B1

(12) United States Patent
Hess et al.

(10) Patent No.: US 6,281,346 B1
(45) Date of Patent: Aug. 28, 2001

(54) RAT OB-RECEPTORS AND NUCLEOTIDES ENCODING THEM

(75) Inventors: John W. Hess, Lansdale, PA (US); C. Thomas Caskey, Houston, TX (US); Qingyun Liu, North Wales; Michael Sean Phillips, Lansdale, both of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 08/803,346

(22) Filed: Feb. 20, 1997

Related U.S. Application Data

(60) Provisional application No. 60/013,969, filed on Mar. 22, 1996.

(51) Int. Cl.[7] .................................................. C12N 15/12
(52) U.S. Cl. ........................ 536/23.5; 435/7.2; 435/69.1; 435/252.3; 435/320.1
(58) Field of Search .................................... 435/7.2, 69.1, 435/252.3, 334, 361, 366, 320.1; 536/23.5

(56) References Cited

U.S. PATENT DOCUMENTS 5,643,748   7/1997   Snodgrass et al. .

FOREIGN PATENT DOCUMENTS

| WO 96/08510 | 3/1996 | (WO) . |
| WO 96/35787 | 11/1996 | (WO) . |
| 9726335 * | 7/1997 | (WO) . |

OTHER PUBLICATIONS

Iida et al *BBRC* 222 1996, p. 19–26.*
Bennett et al, *Current Biology* 6(9) 1996, p. 1170–80.*
Phillips, Michael S., et al. "Leptin receptor missense mutation in the fatty Zucker rat", 1996, Nature Genetics, vol. 13, No. 1, pp. 18–19.
Murakami, Takashi, et al. "Cloning of Rat Obese cDNA and its Expression in Obese Rats+", 1995 Biochem and Biophy., No. 3, pp. 944–952.
Guan et al., "Differential Expression of mRNA for Leptin Receptor Isoforms in the Rat Brain", Molec. and Cell Endocrinology, vol. 133, pp. 1–7, 1997.

Chen et al. "Evidence That the Diabetes Gene Encodes the Leptin Receptor: Identification of a Mutation in the Leptin Receptor Gene in db/db Mice," 1996 Cell 84:491–495.
Chua et al. "Phenotypes of mouse diabetes and rat fatty due to mutations in the OB (leptin) receptor," 1996 Science 271:994–996.
Chua et al. "Phenotype of fatty due to Gln269Pro mutation in the leptin receptor (Lepr)," 1996 Diabetes 45:1141–1143.
Lee et al. "Abnormal splicing of the leptin receptor in diabetic mice", 1996 Nature 379:632–635.
Phillips et al. "Leptin receptor missense mutation in the fatty Zucket rat", 1996 Nature Genetics 13:19–20.
Rosenblum et al. "Functional STAT 1 and 3 signaling by the leptin receptor (OB–R): reduced expression of the rat fatty leptin receptor in transfected cells", 1996 Endocrinology 137:5178–5181.
Spiegelman et al. "Adipogenesis and Obesity: Rounding out the big picture", 1996 Cell 87:377–389.
Stephens et al. "The role of neuropeptide Y in the antiobesity action of the obese gene product", 1995 Nature 377:530–532.
Takaya et al. "Molecular cloning of rat leptin receptor isoform complementary DNAs—identification of a missense mutation in Zucker fatty (fa/fa) rats", 1996 Biochem Biophys Res Comm 225:75–83.
Tartaglia et al. "Identification and Expression Cloning of a Leptin Receptor, OB–R", 1995 Cell 83:1263–1271.
Wang et al. "A novel leptin receptor isoform in rat", 1996 FEBS Lett. 392:87–90.

\* cited by examiner

*Primary Examiner*—John Ulm
(74) *Attorney, Agent, or Firm*—Anna L. Cocuzzo; Jack L. Tribble

(57) ABSTRACT

The rat ob receptor gene has been isolated and cloned. Two different alleles have been identified: the wild-type, and the fa-allele which differs from the wild type by only one base pair. The base pair change, however introduces an MspI restriction site into the DNA sequence, and also results in an amino acid change. Also part of the invention are the receptors, vectors containing the nucleic acid encoding the receptors, host cells transformed with this gene, and assays which use the gene or protein and identify new ligands.

16 Claims, 13 Drawing Sheets

1   MTCQKFYVVL LHWEFLYVIT ALNLAYPTSP WRFKLFCAPP STTDDSFLSP
51  AGVPNNTSSL KGASEALVEA KFNSTGIYVS ELSKTIFHCC FGNEQGQNCS
101 ALTGNTEGKT LASVVKPLVF RQLGVNWDIE CWMKGDLTLF ICHMEPLLKN
151 PFKNYDSKVH LLYDLPEVID DLPLPPLKDS FQTVQCNCSV RECECHVPVP
201 RAKVNYALLM YLEITSAGVS FQSPLMSLQP MLVVKPDPPL GLRMEVTDDG
251 NLKISWDSQT KAPFPLQYQV KYLENSTIVR EAAEIVSDTS LLVDSVLPGS
301 SYEVQVRSKR LDGSGVWSDW SLPQLFTTQD VMYFPPKILT SVGSNASFCC
351 IYKNENQTIS SKQIVWWMNL AEKIPETQYN TVSDHISKVT FSNLKATRPR
401 GKFTYDAVYC CNEQACHHRY AELYVIDVNI NISCETDGYL TKMTCRWSPS
451 TIQSLVGSTV QLRYHRRSLY CPDNPSIRPT SELKNCVLQT DGFYECVFQP
501 IFLLSGYTMW IRINHSLGSL DSPPTCVLPD SVVKPLPPSN VKAEITINTG
551 LLKVSWEKPV FPENNLQFQI RYGLNGKEIQ WKTHEVFDAK SKSASLPVSD
601 LCAVYVVQVR CRRLDGLGYW SNWSSPAYTL VMDVKVPMRG PEFWRIMDGD

FIG.1A

```
 651  ITKKERNVTL  LWKPLMKNDS  LCSVRRYVVK  HRTAHNGTWS  QDVGNQTNLT
 701  FLWAESAHTV  TVLAINSIGA  SLVNFNLTFS  WPMSKVNAVQ  SLSAYPLSSS
 751  CVILSWTLSP  NDYSLLYLVI  EWKNLNDDDG  MKWLRIPSNV  NKYYIHDNFI
 801  PIEKYQFSLY  PVFMEGVGKP  KIINGFTKDD  IAKQQNDAGL  YVIVPIISS
 851  CVLLLGTLLI  SHQRMKKLFW  DDVPNPKNCS  WAQGLNFQKP  ETFEHLFTKH
 901  AESVIFGPLL  LEPEPVSEEI  SVDTAWKNKD  EMVPAAMVSL  LLTTPDSTRG
 951  SICISDQCNS  ANFSGAQSTQ  GTCEDECQSQ  PSVKYATLVS  NVKTVETDEE
1001  QGAIHSSVSQ  CIARKHSPLR  QSFSSNSWEI  EAQAFFLLSD  HPPNVISPQL
1051  SFSGLDELLE  LEGNFPEENH  GEKSVYYLGV  SSGNKRENDM  LLTDEAGVLC
1101  PFPAHCLFSD  IRILQESCSH  FVENNLNLGT  SGKNFVPYMP  QFQSCSTHSH
1151  KIIENKMCDL  TV
```

FIG.1B

```
  1  TGGGGCAATT GGGCTGACCT TTCTTATGCT GGGATGTGCC TTGGAGGACT
 51  ATGGGTGTCT ATCTCTGAAG TAAGATGACG TGTCAGAAAT TCTATGTGT
101  TTTGTTACAC TGGGAATTTC TGTATGTGAT AACTGCACTT AACCTGGCCT
151  ATCCAACCTC TCCCTGGAGA TTTAAGCTGT TTTGTGCGCC ACCGAGTACA
201  ACTGATGACT CCTTTCTCTC TCCTGCTGGA GTCCCAAACA ATACTTCGTC
251  TTTGAAGGGG GCTTCTGAAG CACTTGTTGA AGCTAAATTT AATTCAACTG
301  GTATCTACGT TTCTGAGTTA TCCAAAACCA TTTTCCACTG TTGCTTTGGG
351  AATGAGCAAG GTCAAAACTG CTCCGCACTC ACAGGCAACA CTGAAGGGAA
401  GACGCTGGCT TCAGTGGTGA AGCCTTTAGT TTTCCGCCAA CTAGGTGTAA
451  ACTGGGACAT AGAGTGCTGG ATGAAAGGGG ACTTGACATT ATTCATCTGT
501  CATATGGAAC CATTACTTAA GAACCCCTTC AAGAATTATG ACTCTAAGGT
551  TCACCTTTTA TATGATCTGC CTGAAGTTAT AGATGATTTG CCTCTGCCCC
601  CACTGAAAGA CAGCTTTCAG ACTGTCCAGT GCAACTGCAG TGTTCGGGAA
```

FIG. 2A

| | | | | |
|---|---|---|---|---|
| 651 | TGCGAATGTC | ATGTACCAGT | ACCCAGAGCC | AAAGTCAACT | ACGCTCTTCT |
| 701 | GATGTATTTA | GAAATCACAT | CTGCTGGTGT | GAGTTTTCAG | TCACCTCTAA |
| 751 | TGTCACTGCA | GCCCATGCTT | GTTGTGAAGC | CCGATCCACC | GCTGGGTTTG |
| 801 | CGTATGGAAG | TCACAGATGA | TGGTAATTTA | AAGATTTCAT | GGGACAGCCA |
| 851 | AACAAAAGCA | CCATTTCCAC | TTCAATATCA | GGTGAAATAT | TTAGAGAATT |
| 901 | CTACAATCGT | AAGAGAGGCT | GCTGAAATCG | TCTCGGATAC | ATCTCTGCTG |
| 951 | GTAGACAGCG | TGCTTCCTGG | GTCTTCATAC | GAGGTCCAGG | TGAGGAGCAA |
| 1001 | GAGACTGGAT | GGCTCAGGAG | TCTGGAGTGA | CTGGAGTTTA | CCTCAACTCT |
| 1051 | TTACCACACA | AGATGTCATG | TATTTTCCAC | CCAAAATTCT | GACGAGTGTT |
| 1101 | GGATCCAATG | CTTCCTTTTG | CTGCATCTAC | AAAAATGAGA | ACCAGACTAT |
| 1151 | CTCCTCAAAA | CAAATAGTTT | GGTGGATGAA | TCTAGCCGAG | AAGATCCCCG |
| 1201 | AGACACAGTA | CAACACTGTG | AGTGACCACA | TTAGCAAAGT | CACTTTCTCC |
| 1251 | AACCTGAAAG | CCACCAGACC | TCGAGGGAAG | TTTACCTATG | ATGCAGTGTA |
| 1301 | CTGCTGCAAT | GAGCAGGCAT | GCCATCACCG | CTACGCTGAA | TTATATGTGA |

FIG.2B

| | | | | | |
|---|---|---|---|---|---|
| 1351 | TCGATGTCAA | TATCAATATA | TCATGTGAAA | CTGACGGGTA | CTTAACTAAA |
| 1401 | ATGACTTGCA | GATGGTCACC | CAGCACAATC | CAATCACTAG | TGGGAAGCAC |
| 1451 | TGTGCAGTTG | AGTATCACA  | GGCGCAGCCT | GTACTGTCCC | GATAATCCAT |
| 1501 | CTATTCGTCC | TACATCAGAG | CTCAAAAACT | GCGTCTTACA | GACAGATGGC |
| 1551 | TTTTATGAAT | GTGTTTTCCA | GCCAATCTTT | CTATTATCTG | GCTATACAAT |
| 1601 | GTGGATCAGG | ATCAACCATT | CTTTAGGTTC | ACTTGACTCT | CCACCAACGT |
| 1651 | GTGTCCTTCC | TGACTCCGTA | GTAAAACCAC | TACCTCCATC | TAATGTAAAA |
| 1701 | GCAGAGATTA | CTATAAACAC | TGGATTATTG | AAAGTATCTT | GGGAAAAGCC |
| 1751 | AGTCTTTCCA | GAGAATAACC | TTCAGTTCCA | GATTCGATAT | GGCTTAAATG |
| 1801 | GAAAAGAAAT | ACAATGGAAG | TATTCGATGC | AAAATCAAAA |
| 1851 | TCGGCCAGCC | TGCCAGTGTC | AGATCTCTGT | GCGGTCTATG | TGGTACAGGT |
| 1901 | TCGCTGCCGG | CGGTTGGATG | GACTAGGGTA | TTGGAGTAAT | TGGAGCAGTC |
| 1951 | CAGCCTACAC | TCTTGTCATG | GATGTAAAAG | TTCCTATGAG | AGGGCCTGAA |

FIG.2C

```
2001  TTCTGGAGAA TAATGGATGG GGATATTACT AAAAAGGAGA GAAATGTCAC
2051  CTTGCTTTGG AAGCCACTGA TGAAAAATGA CTCACTGTGT AGTGTGAGGA
2101  GGTATGTGGT GAAGCATCGT ACTGCCCACA ATGGGACATG GTCACAAGAT
2151  GTGGAAATC  AGACCAATCT CACTTTCCTG TGGCAGAAT  CAGCACACAC
2201  TGTTACAGTT CTGGCCATCA ATTCCATCGG TGCCTCCCTT GTGAATTTTA
2251  ACCTTACGTT CTCATGGCCC ATGAGTAAAG TGAATGCTGT GCAGTCACTC
2301  AGTGCTTATC CCCTGAGCAG CAGCTGCGTC ATCCTTTCCT GGACACTGTC
2351  ACCTAATGAT TATAGTCTGT TATTGAATGG AAGAACCTTA
2401  ATGATGATGA TGGAATGAAG TGGCTTAGAA TCCCTTCGAA TGTTAACAAG
2451  TATTATATCC ATGATAATTT TATTCCTATC GAGAAATATC AGTTTAGTCT
2501  TTACCCAGTA TTTATGGAAG GAGTTGGAAA ACCAAAGATA ATTAATGGTT
2551  TCACCAAAGA TGATATCGCC AAACAGCAAA ATGATGCAGG GCTGTATGTC
2601  ATTGTACCGA TAATTATTTC CTCTTGTGTC CTGCTGCTCG GAACACTGTT
2651  AATTTCACAC CAGAGAATGA AAAAGTTGTT TTGGACGAT  GTTCCAAACC
```

FIG.2D

```
2701  CCAAGAATTG TTCCTGGGCA CAAGGACTTA ATTTCCAAAA GCCTGAAACA
2751  TTTGAGCATC TTTTTACCAA GCATGCAGAA TCAGTGATAT TTGGTCCTCT
2801  TCTTCTGGAG CCTGAACCAG TTTCAGAAGA AATCAGTGTC GATACAGCTT
2851  GGAAAAATAA AGATGAGATG GTACCAGCAG CTATGGTCTC ACTTCTTTTG
2901  ACCACTCCAG ATTCCACAAG GGGTTCTATT TGTATCAGTG ACCAGTGTAA
2951  CAGTGCTAAC TTCTCTGGGG CTCAGAGCAC CCAGGGAACC TGTGAGGATG
3001  AGTGTCAGAG TCAACCCTCA GTTAAATATG CAACGCTGGT CAGCAACGTG
3051  AAAACAGTGG AAACTGATGA AGAGCAAGGG GCTATACATA GTTCTGTCAG
3101  CCAGTGCATC GCCAGGAAAC ATTCCCCACT GAGACAGTCT TTTTCTAGCA
3151  ACTCCTGGGA GATAGAGGCC CAGGCATTTT TCCTTTTATC AGATCATCCA
3201  CCCAATGTGA TTTCACCACA ACTTTCATTC TCAGGGTTGG ATGAGCTTTT
3251  GGAACTGGAG GGAAATTTTC CTGAAGAAAA TCACGGGGAA AAATCTGTGT
3301  ATTATCTAGG AGTCCCTCA GGAAACAAAA GAGAGAATGA TATGCTTTTG
```

FIG.2E

```
3351   ACTGATGAGG CAGGGGTATT GTGCCCATTC CCAGCTCACT GTCTGTTCAG
3401   TGACATCAGA ATCCTCCAGG AGAGTGTTC ACACTTTGTA GAAAATAATT
3451   TGAATTTAGG GACCTCTGGT AAGAACTTTG TACCTTACAT GCCCCAGTTT
3501   CAATCCTGTT CCACTCACAG TCATAAGATA ATAGAAAATA AGATGTGTGA
3551   CTTAACTGTG TAATCTTGTC CAAAACTTC CAGGTTCCAT TCCAGTAGAG
3601   TGTGTCATGT ATAATATGTT CTTTTATAGT TGTGGGTGGG AGAGAAAGCC
```

FIG.2F

F=FORWARD  R=REVERSE

| PRIMER NAME | LOCATION IN RAT cDNA | OLIGO SEQUENCE | NOTES |
|---|---|---|---|
| ROBR 1 | 75-93 F | ATG ATG TG(C/T) CA(A/G) AA(A/G) TT(C/T) T | DEGENERATE TO MOUSE SEQUENCE |
| ROBR 2 | 108-127 F | CA(C/T) TGG GA(A/G) TT(C/T) CTI TA(C/T) GT | DEGENERATE TO MOUSE SEQUENCE |
| ROBR 3 | 462-478 F | GA(A/G) TG(T/C) TGG ATG AA(A/G) GG | DEGENERATE TO MOUSE SEQUENCE |
| ROBR 4 | 1158-1175 F | AA(A/G) CA(A/G) ATI GTI TGG TGG | DEGENERATE TO MOUSE SEQUENCE |
| ROBR 5 | 1590-1606 F | GGI TA(T/C) ACI ATG TGG AT | DEGENERATE TO MOUSE SEQUENCE |
| ROBR 6 | 1606-1590 R | ATC CAC ATI GT(A/G)TAI CC | DEGENERATE TO MOUSE SEQUENCE |
| ROBR 7 | 1945-1926 R | CTC CA(A/G) TT(A/G) CTC CA(A/G) TAI CC | DEGENERATE TO MOUSE SEQUENCE |
| ROBR 8 | 2282-2275 R | AC(T/C) TT(A/G) CTC ATI GGC CA | DEGENERATE TO MOUSE SEQUENCE |
| ROBR 9 | 2263-2045 R | CCA (T/C)TT CAT ICC (A/G)TC (A/G)TC | DEGENERATE TO MOUSE SEQUENCE |
| ROBR 10 | 133-153 F | CTG CAC TTA ACC TGG CCT ATC | RAT SPECIFIC PRIMER |
| ROBR 11 | 153-133 R | GAT AGG CCA GGT TAA GTG CAG | RAT SPECIFIC PRIMER |
| ROBR 12 | 380-361 R | GAG TGC GGA GCA GTT TTG AC | RAT SPECIFIC PRIMER |
| ROBR 13 | 930-951 F | GTC TCG GAT ACA TCT CTG CTG G | RAT SPECIFIC PRIMER |
| ROBR 14 | 1435-1427 R | GAT TGG ATT GTG CTG GGT G | RAT SPECIFIC PRIMER |
| ROBR 15 | 2047-2065 F | TCA CCT TGC TTT GGA AGC C | RAT SPECIFIC PRIMER |
| ROBR 16 | 2135-2155 F | GAC ATG GTC ACA AGA TGT GGG | RAT SPECIFIC PRIMER |
| ROBR 17 | 2216-2196 R | GGC CAG AAC TGT AAC AGT GTG | RAT SPECIFIC PRIMER |
| ROBR 18 | 435-455 F | CGC CAA CTA GGT GTA AAC TGG | RAT SPECIFIC PRIMER |
| ROBR 19 | 813-794 R | TGA CTT CCA TAC GCA AAC CC | RAT SPECIFIC PRIMER |
| ROBR 20 | 1444-1463 F | GAA GCA CTG TGC AGT TGA GG | RAT SPECIFIC PRIMER |
| ROBR 21 | 1815-1835 F | GGA AGA CAC ACG AGG TAT TCC | RAT SPECIFIC PRIMER |
| ROBR 22 | 673-693 F | CCA GAG CCA AAG TCA ACT ACG | RAT SPECIFIC PRIMER |
| ROBR 23 | 2338-2358 F | CCT GGA CAC TGT CAC CTG ATG | RAT SPECIFIC PRIMER |
| ROBR 24 | R | CAT(T/C)TC (A/G)TC (T/C)TT (A/G)TT(T/C)TT CCA | DEGENERATE TO MOUSE C-TERMINUS |

FIG.3A

| | | | |
|---|---|---|---|
| ROBR 25 | R | TC(A/G) CAC AT(T/C) TT(A/G) TT(T/C) TTC CA | DEGENERATE TO MOUSE C-TERMINUS |
| ROBR 26 | R | AA(T/C) TGI GGC AT(A/G) TAI CC | DEGENERATE TO MOUSE C-TERMINUS |
| ROBR 27 | 796-816 F | GTT TGC GTA TGG AAG TCA CAG | RAT SPECIFIC PRIMER |
| ROBR 28 | 952-932 R | ACC AGC AGA GAT GTA TCC GAG | RAT SPECIFIC PRIMER |
| ROBR 29 | 2531-2548 F | CTG CTG CTC GGA ACA CTG | RAT SPECIFIC PRIMER |
| ROBR 30 | 2897-2874 R | AAG TGA GAC CAT AGC TGC TGG | RAT SPECIFIC PRIMER |
| ROBR 31 | 771-789 F | CTT CTG AAG CCC GAT CCA C | RAT SPECIFIC PRIMER |
| ROBR 33 | R | GGG ACA AAA TTA CAC AGT TAA TTC ACA C | RAT SPECIFIC PRIMER |
| ROBR 34 | 2603-2583 R | AAT GAC ATA CAG CCC TGC ATC | RAT SPECIFIC PRIMER |
| ROBR 35 | 41-59 F | TTG GAC TAT GGG TGT C | RAT SPECIFIC PRIMER |
| ROBR 36 | 3511-2493 R | GAA CAG GAT TGA AAG TGG G | RAT SPECIFIC PRIMER |
| ROBR 37 | 3598-3580 R | CTA CTG GAA TGG AAC CTG G | RAT SPECIFIC PRIMER |
| ROBR 38 | 646-666 F | GGG AAT GCG AAT GTC ATG TAC | RAT SPECIFIC PRIMER |
| ROBR 39 | 1014-995 R | AGC CAT CCA GTC TCT TGC TC | RAT SPECIFIC PRIMER |
| ROBR 40 | 1417-1435 F | CAC CCA GCA CAA TCC AAT C | RAT SPECIFIC PRIMER |
| ROBR 41 | 1793-1773 R | GCC ATA TCG AAT CTG GAA CTG | RAT SPECIFIC PRIMER |
| ROBR 42 | 2404-2424 F | ATG ATG ATG GAA TGA AGT GGC | RAT SPECIFIC PRIMER |
| ROBR 43 | 3110-3091 R | GAT GCA CTG GCT GAC AGA AC | RAT SPECIFIC PRIMER |
| ROBR 44 | 3091-3110 F | GTT CTG TCA GCC AGT GCA TC | RAT SPECIFIC PRIMER |
| ROBR 45 | 687-667 R | TGA CTT TGG CTC TGG GTA CTG | RAT SPECIFIC PRIMER |
| ROBR 46 | 2010-1991 R | TTC TCC AGA ATT CAG GCC CT | RAT SPECIFIC PRIMER |
| ROBR 47 | 2807-2826 F | GGA GCC TGA ACC AGT TTC AG | RAT SPECIFIC PRIMER |
| ROBR 48 | | TTT GAC TGA GGC AGG G | RAT SPECIFIC PRIMER |

FIG.3B

| | | |
|---|---|---|
| HOBR 1F | CTT ATG CTG GGA TGT GCC | HUMAN SPECIFIC 5' UTR PRIMER |
| HOBR 1F-2 | TCG TGG CAT TAT CCT TCA G | HUMAN SPECIFIC 5' UTR PRIMER |
| HOBR 1R | TCT CTC CCA CCC ACA ACT AT | HUMAN SPECIFIC 3' UTR (OB-Rb) PRIMER |
| HOBR 5 | CAT CAT (T/C)TC (A/G)TC (T/C)TT (A/G)TT (T/C)TT CCA | DEGENERATE TO HUMAN C-TERMINUS |
| HOBR 6 | GT(T/C) TG(A/G) AA(T/C) TGT GGC AT | DEGENERATE TO HUMAN C-TERMINUS |
| HOBR 7 | TC(A/G) CAC AT(T/C) TT(A/G) TT(T/C) TCC AT | DEGENERATE TO HUMAN C-TERMINUS |
| MOBR 1F | GTT CTG CAA ATC CAG GTG TA | MOUSE SPECIFIC 5' UTR PRIMER |
| MOBR 1R | TGG GTT CAT CTG TAG TGG TC | MOUSE SPECIFIC 3' UTR (OB-Ra) PRIMER |

RAT OB-RECEPTORS AND NUCLEOTIDES ENCODING THEM

This application claims benefit of Provisional Appln. 60/013,969 filed Mar. 22, 1996.

FIELD OF THE INVENTION

This invention relates to rat ob receptor proteins, to DNA and RNA sequences encoding them, and to assays using rat receptor proteins.

BACKGROUND OF THE INVENTION

Recently the identification of mutations in several genes involved in the onset of obesity in rodents have been identified. Of particular interest are mutations discovered in the peptide hormone, leptin, which is a component of a novel signal transduction pathway that regulates body weight (Zhang et al. 1994, *Nature* 372:425–432; Chen et al. 1996, *Cell* 84:491–495). Leptin was initially discovered by the positional cloning of the obesity gene, ob, in mice. Two different ob alleles have been identified: one mutation causes the premature termination of the leptin peptide resulting in a truncated protein, and the other mutation changes the transcriptional activity of the obesity (ob) gene, resulting in a reduced amount of circulating leptin.

There is a correlation between a decrease in the levels of biologically active leptin and the overt obese phenotype observed in ob/ob mice. Recombinant leptin has been shown to induce weight loss in the ob/ob mouse but not in the diabetic phenotype db/db mouse (Campfield et al. 1995, *Science* 269: 546–549; Halaas et al. 1995, *Science* 269: 543–546; Pellymounter et al. 1995, *Science* 269:540–543; Rentsch et al. 1995, *Biochem. Biophys. Res. Comm.* 214:131–136; and Weigle et al. 1995, *J. Clin. Invest.* 96:2065–2070).

Although the synthesis of leptin occurs in the adipocyte, its ability to decrease food intake and increase metabolic rate appears to be mediated centrally by the hypothalamus. Injection of recombinant leptin into the third ventricle of the brain elicits a similar response as peripheral administration of leptin. Furthermore, the recent cloning of the human receptor for the leptin, the ob-receptor (OB-R), reveals that it is transcribed in the hypothalamus (Tartaglia et al. 1995, *Cell* 83:1263–1271; Stephens et al. 1995, *Nature* 377: 530–532). In addition, a mutation that results in premature termination of the long-form of the mouse OB-R, which is preferentially expressed in the hypothalamus, appears to be responsible for the obese phenotype of the db/db mouse (Lee et al. 1996, *Nature* 379:632–635; Chua et al. 1996, *Science* 271:994–996; and Chen et al. 1996, *Cell* 84:491–495).

The fa mutation is a recessive allele that arose spontaneously in the 13M rat strain and was first reported in 1961 (Zucker et al. 1961, *J. Heredity* 52: 275–278. The onset of obesity in the fa/fa Zucker rat is at 5–7 weeks of age and progresses with age. The mature fatty rat is approximately twice the weight of lean litter mates and over 40% of its body weight is adipose tissue (Zucker et al. 1962, *Proc. Soc. Exp. Biol. Med.* 110:165–171; Zucker et al. 1963, *J. Nutrition* 80:6–19). The fa/fa Zucker rat exhibits hypercholesterolemia, hyperlipemia, and hyperglycemia and has been used extensively as an animal model for human cardiovascular disease and diabetes. Most of the fatty Zucker rat colonies have been maintained by outbreeding in order to retain heterozygousity at as many loci as possible. However, certain stocks have been inbred to produce animals such as the Zucker diabetic fatty (ZDF) rat which exhibits a more profound diabetic phenotype than the outbred fa/fa Zucker rat (Clark, et al. 1983, *Proc. Soc. Exp. Biol. Med.* 173: 68–75).

The fa mutation maps to rat chromosome 5 in a region that is syntenic with the db allele on mouse chromosome 4 (Truett, et al. 1991, *Proc. Natl. Acad. Sci.* 88: 7806–7809). This observation, in conjunction with the similar phenotypes of the fa/fa rat and the db/db mouse, led to the proposal that the fa gene was the rat homologue of the db gene. Higher resolution genetic mapping supports the contention that the fa mutation is located in the gene encoding the rat OB-R (Chua et al. *Science* 271: 994).

It would be desirable to be able to further experiment with the rodent model system for obesity, and to be able to clone and produce purified rat ob receptor to use in assays for the identification of ligands which may be useful in understanding obesity and for its prevention and treatment.

DETAILED DESCRIPTION OF THE INVENTION

This invention relates to a rat ob receptor which is substantially free from associated rat membrane proteins. It also relates to substantially purified rat ob receptor ("rat OB-R" or "rat OB-receptor") protein. One of the rat OB-Rs of this invention is obtained from a rat which has a wild-type OB-R. Another rat OB-R of this invention is obtained from a rat which has the fa mutation.

Another aspect of this invention is to nucleic acids which encode a rat OB receptor. The nucleic acid may be any nucleic acid which can encode a protein, such as genomic DNA, cDNA, or any of the various forms of RNA. Preferably, the nucleic acid is cDNA.

This invention also includes vectors containing a rat OB-R gene, host cells containing the vectors, and methods of making susbstantially pure rat OB-R protein comprising the steps of introducing a vector comprising a rat OB-R gene into a host cell, and cultivating the host cell under appropriate conditions such that rat OB-R is produced. The rat OB-R so produced may be harvested from the host cells in conventional ways.

Yet another aspect of this invention are assays which employ a rat OB-R. In these assays, various molecules, suspected of being rat OB-R ligands are contacted with a rat OB-R, and their binding is detected. In this way agonists, antagonists, and ligand mimetics may be identified. A further aspect of this invention are the ligands so indentified.

BRIEF DESCRIPTION OF THE FIGURES

FIGS. 1A–1B illustrate the amino acid sequence of the rat OB-receptor.

FIGS. 2A–2F illustrate the cDNA sequence of the rat OB receptor.

FIGS. 3A–3C illustrate a table of primers used for the PCR reactions detailed in the Examples.

Figure 5:
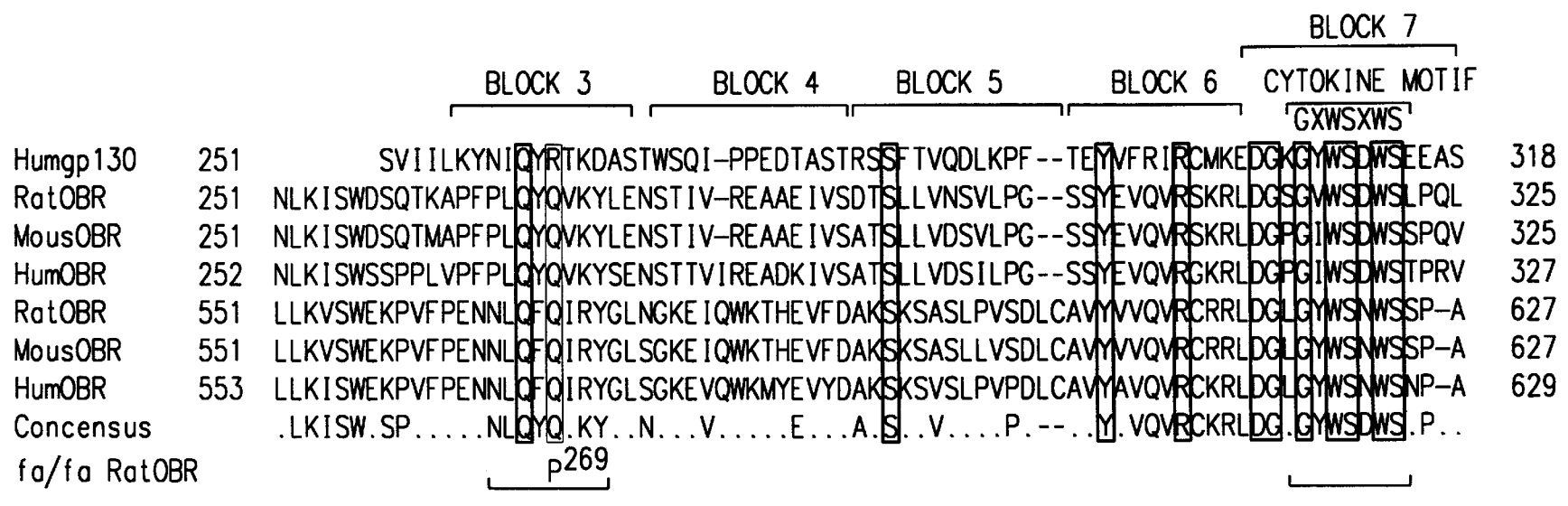

FIG. 5 compares the amino acid sequence between human cytokine receptor gp130 (Humgp 130), the mouse OB-R (MousOBR), human OB-R (HumOBR) and lean rat OB-R (RatOBR). The numbering refers to the location in the protein, and the cytokine motif GXWSXWS (SEQ ID NO:66) can be seen.

Figure 4B:
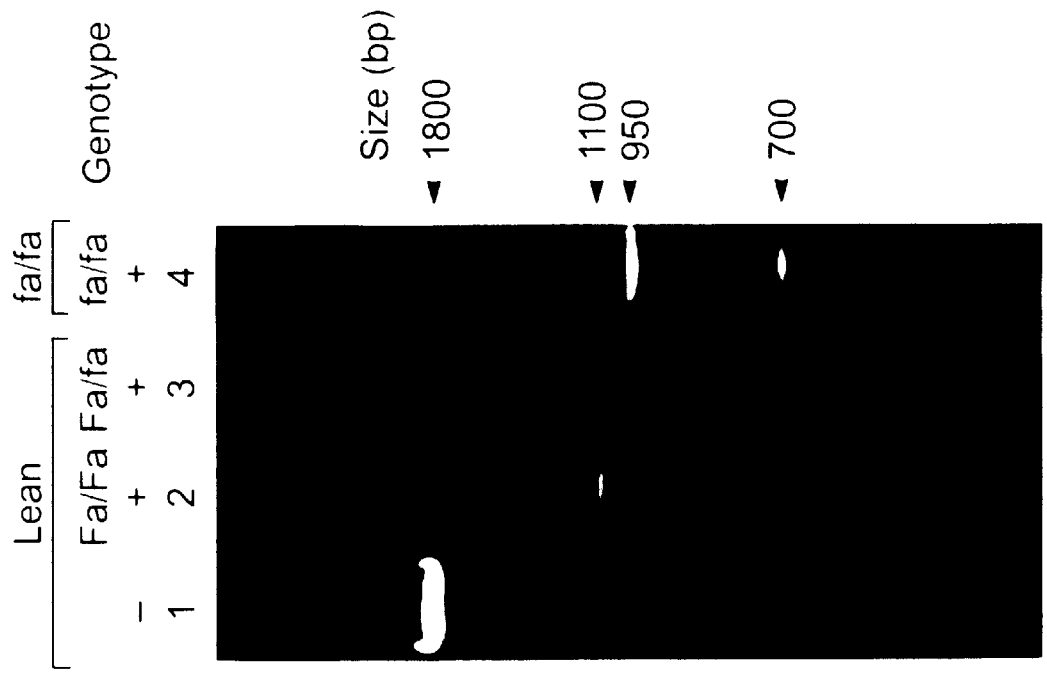
FIGS. 4A–4B illustrate the gels demonstrating the analysis of the $A^{880}$ to C mutation identified in the OB-receptor from hypothalamic cDNA and genomic DNA obtained from lean and fa/fa rats.
Figure 4A:
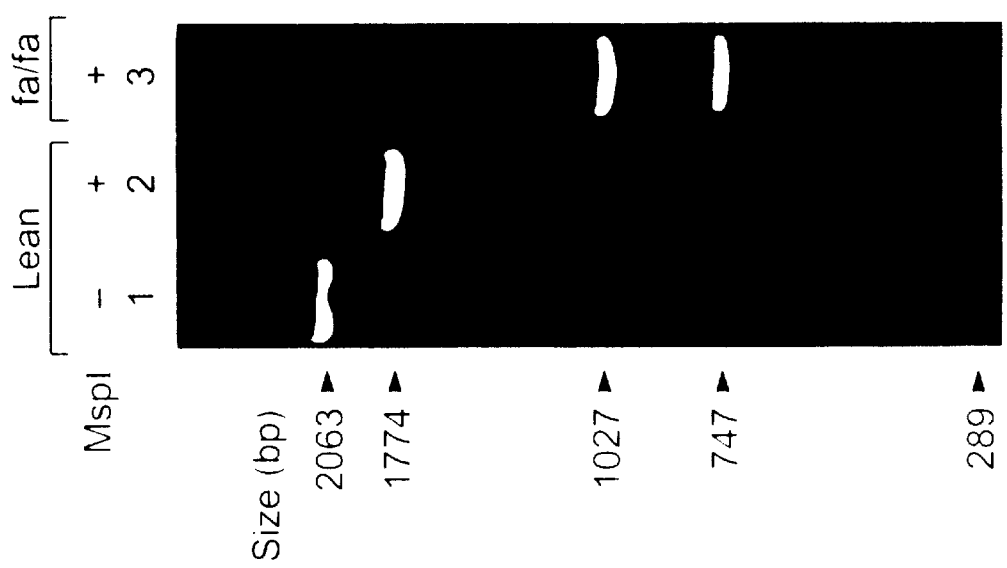

As used througout the specification and claims, the following definitions apply:

"Substantially free from associated rat membrane proteins" means that the rat receptor protein is not in physical contact with any rat membrane proteins.

"Substantially purified rat OB-receptor" means that the rat receptor protein is at least 90% and preferably at least 95% pure.

"Wild type" means that the gene or protein is substantially the same as that found in a rat which is not considered to have a mutation for that gene or protein. It is also referred to as "lean" throughout the specification and claims.

"fa" means that the gene or protein is substantially the same as that found in a rat homologous for the fatty mutation.

"Substantially the same" when referring to a nucleic acid or amino acid sequence means either it is the same as the reference sequence, or if not exactly the same, contains changes which do not affect its biological activity or function. Although the fa and wild type rat OB-R genes differ by only one nucleotide, they are not considered "substantially the same" as the biological activity and functions of their encoded proteins are very different.

The rat OB-R is a member of the cytokine receptor family. Motifs that are characteristic of the cytokine receptors such as the motif WSXWS (SEQ ID NO:67 W is the amino acid residue tryptophan, S is the amino acid residue serine and X is any amino acid.) were found to be conserved in the rat OB-R.

One aspect of this invention is the molecular cloning of a rat OB-R. The nucleotide sequence for the rat OB-R from both lean and fa/fa rat hypothalamic cDNA was determined and compared. In the fa/fa rat, there was a single nucleotide change, an A to C at nucleotide 880 resulting in an amino acid change at glutamine 269 to proline. The mutation introduces an Msp I site (CCGG) that was utilized to genotype a number of lean control and fatty animals. The results indicate that the mutation is tightly linked to the fa allele. Thus, it is likely that the fa mutation lies in the OB-R receptor cDNA and that the A to C transversion at base pair 880 is responsible for the obese phenotype. Both rat OB-R alleles, i.e. the OB-R containing a glutamine 269 and the allele containing proline 269 are part of this invention, as are all nucleic acids which can encode them.

The nucleotide sequence of the wild type rat OB-R cDNA obtained in accordance with this invention has 3650 nucleotides, as shown in FIGS. 2A–2F. This DNA sequence contains an open reading frame from nucleotide 75 to 3563 that encodes a protein of 1162 amino acids. The open reading frame extending from nucleotide 75 to 3563 makes up one aspect of this invention.

The wild type and fa receptor proteins contain an extracellular, a transmembrane domain and a cytoplasmic domain. The extracellular domain extends from amino acids 1–830; the transmembrane domain is from amino acids 839–860; and the cytoplasmic domain is from amino acids 860–1162. This invention also includes proteins which lack one or more of these domains. Such deleted proteins are useful in assays for identifying ligands and their binding activity.

It has also been found that alternate splicing can occur in the receptor gene processing. This can occur at base pair 2742 (lysine$^{889}$). The alternative sequence (for both the wild type and fa) genes and receptors (SEQ ID Nos: 68 and 69, respectively) is shown below and forms another aspect of this invention:

```
AGA GCG GAC ACT CTT TGA ATA TCT
 R   A   D   T   L  STOP
```

Amino acids 1–28 form a signal sequence; thus the mature proteins extend from amino acids 28–1162. The mature proteins form yet another aspect of this invention. This differs from the signal sequence of 1–22 reported for mouse and human OB-r; this may be explained by the use of a different analysis program.

Comparison of wild type rat OB-R to known OB-R receptors of different species has revealed some similarities. For example, the rat OB-R nucleotide sequence is 93% identical to the mouse OB-R and 81% identical to the human OB-R sequences. The deduced amino acid sequence of the rat OB receptor is 93% identical to the mouse and 76% identical to the human OB-R.

The size of the open reading frame of the rat OB-receptor of this invention, (1162 amino acids) is similar to that of the human OB-R (1165 amino acids) reported by Toriaglla et al. 1995, Cell 83:1–20. Both the rat OB-R of this invention and the human OB-R contain a large cytoplasmic domain. In contrast, the mouse OB-receptor of 894 amino acids has a relatively short cytoplasmic domain.

One of the most notable and surprising aspects of this invention is that there is only a single nucleotide difference between the wild type rat cDNA and the fa/fa rat cDNA for the OB-R. PCR fragments obtained from fa/fa cDNA were sequenced. A single nucleotide change relative to the lean cDNA sequence was observed in the hypothalamus. An A to C transversion at bp 880 results in an amino acid change of glutamine to proline at amino acid residue 269. Every tissue examined in the fa/fa rat was found to be homozygous for this A to C mutation at nucleotide 880. The A to C change in the sequence introduces a MspI restriction endonuclease site (CCGG) into the sequence, and this is the basis of an assay for presence of the mutation.

Thus another aspect of this invention is an assay to determine the genotype of a OB-R DNA, suspected of having an A to C mutation at bp 880, comprising digesting the OB-R DNA with MspI, and comparing the restriction products so producted. In a preferred embodiment, the assay comprises generating PCR products of the OB-R DNA, digesting the PCR products with MspI, and comparing the restriction products so produced with those obtained from a rat containing a wild-type OB-R gene. The gene from a rat which has a wild-type OB-R will yield two restriction products, 1774 and 289 bp long. The gene from the fa rat will have three restriction products: 747, 1027 and 289 bp long. These are easily observed using standard gel techniques.

The OB-R gene can be introduced into virtually any host cell using known vectors. Preferred host cells include E. coli as well as mammalian and yeast cell lines.

One of ordinary skill in the art is able to choose a known vector which is appropriate for a given host cell; generally plasmids or viral vectors are preferred. The OB-R gene may be present in the vector in its native form, or it may be under the control of a heterologous promoter, and if desired, one or more enhancers, or other sequences known to regulate transcription or translation. The host cell containing the OB-R gene is cultured, and the OB-R gene is expressed. After a suitable period of time the OB-R protein may be harvested from the cell using conventional separation techniques.

A further aspect of this invention is the use of rat OB-R in assays to identify OB-R ligands. A ligand binds to the OB-R, and in vivo may or may not result in an activation of the receptor. Ligands may be agonists of the receptor (i.e. stimulate its activity), antagonists (inhibit its activity) or they may bind with little or no effect upon the receptor activity.

In an assay for ligands, the rat OB-R of this invention is exposed to a putative ligand, and the amount of binding is measured. The amount of binding may be measured in many ways; for example, a ligand or the OB-R being investigated may be labeled with a conventional label (such as a radioactive or fluorescent label) and then put in contact with the OB-R under binding conditions. After a suitable time, the unbound ligand is saparated from the OB-R and the amount of ligand which has bound can be measured. This can be performed with either the wild-type OB-R or the fa OB-R of this invention; alternatively the amount of binding to the two alleles can be compared. In a competitive assay, both the putative ligand and a known ligand are present, and the amount of binding of the putative ligand is compared to the amount of binding to a known ligand. Alternatively, the putative ligand's ability to displace previously bound known ligand (or vice-versa) may be measured. In yet other embodiments, the assay may be a heterogeneous one, where the OB-R may be bound to a surface, and contacted with putative ligands. Dectection of binding may be by a variety of methods, including labelling, reaction with antibodies, and chomophores.

The following non-limiting Examples are presented to better illustrate the invention.

EXAMPLE 1

Preparation of mRNA and cDNA From Rat Tissues

Tissues were collected from lean and fa/fa Zucker rats and snap frozen in liquid nitrogen. The tissues collected included: hypothalamus, pituitary, lung, liver, kidney, heart, adrenal glands, smooth muscle, skeletal muscle, and adipose tissue. The tissues were homogenized with a Brinkmann Polytron homogenizer in the presence of guanadinium isothiocyanate. mRNA was prepared from hypothalamus, lung, and kidney according to the instructions provided with the messenger RNA isolation kit (Stratagene, La Jolla, Calif.). cDNA was prepared from approximately 2 μg of mRNA with the SuperScript™ choice system (Gibco/BRL Gaithersburg, Md.). The first strand cDNA synthesis was primed using 1 ug of oligo(dT)12–18 primer and 25 ng of random hexamers per reaction. Second strand cDNA sythesis was performed according to the manufacturer's instructions. The quality of the cDNA was assessed by labeling an aliqout ($\frac{1}{10}^{th}$) of the second strand reaction with approximately 1 μCi of [a-$^{32}$P]dCTP (3000 Ci/mmol). The labeled products were separated on an agarose gel and detected by autoradiography.

EXAMPLE 2

Amplification of Lean Rat OB-receptor cDNA using PCR

The initial portion of the rat OB receptor was obtained by PCR using degenerate primers based on the mouse and human OB-receptor amino acid sequences. A set of 9 oligonucleotide primers, ROBR 1–9, shown in FIG. 3A–3C, were designed to regions with low codon degeneracy. The pairing of the forward primers ROBR 2 ('5-CAY TGG GAR TTY CTI TAY GT-3') and ROBR 3 (5'-GAR TGY TGG ATG AAY GG-3'), SEQ ID NOs:4 and 5, respectively, corresponding to mouse amino acid sequences HWEFLYV and ECWMKG(SEQ ID NOs: 70 and 71, respectively), with reverse primers ROBR 6 (5 '-ATC CAC ATI GTR TAI CC-3'), 7(5'-CTC CAR TTR CTC CAR TAI CC-3'), and 8 (5'-ACY TTR CTC ATI GGC CA-3'), SEQ ID NOs:8–10, respectively, representing mouse amino acids, GYTMWI, VYWSNWS, and WPMSKV, (SEQ ID NOs:72–74) respectively) provided good yields of the appropriately sized products. The fragments of interest were amplified as long polymerase chain reaction (PCR) products by a modifying of the method of Barnes (1994, *Proc. Natl. Acad. Sci.* 91:2216–2220, which is hereby incorporated by reference. In order to obtain the required long PCR fragments, Taq Extender (Stratagene, La Jolla Calif.) and the Expand Long Template PCR System (Boehringer Mannheim, Indianapolis, Ind.) were used in combination. The standard PCR reaction mix, in a final volume of 20 μl, contained 5 ng of template (lean rat cDNA), 100 ng of primers, 500 μM dNTPs, 1×Buffer 3 from the Expand kit, 0.1 μl each of Taq Polymerase and Taq Expander. Reactants were assembled in thin walled reaction tubes. The amplification protocol was 1 cycle of 92° C. for 30 sec., followed by 32 cycles at 92° C. for 30 sec., 45° C. for 1 min. and 68° C. for 3 min. using a Perkin-Elmer (Norwalk, Conn.) 9600 Thermal Cycler.

This strategy produced a series of PCR products with the largest being approximately 2.2 Kbp amplified from primers ROBR 2 and ROBR 8. These products were subcloned for DNA sequence analysis as described below.

EXAMPLE 3

Subcloning of PCR Products

PCR products of the appropriate size were prepared for subcloning by separation on an agarose gel, excising the band, and extracting the DNA using Prep-A-Gene (BioRad, Richmond, Calif.). PCR products were ligated into pCR™II (Invitrogen, San Diego, Calif.) according to the instructions provided by the manufacturer. The ligation was transformed into INVaF cells and plated on Luria-Bertani plates containing 100 μg/ml ampicillin and X-Gal (32 μl of 50 mg/ml X-Gal (Promega, Madison, Wis.). White colonies were picked and grown overnight in Luria -Bertani broth plus 100 μg/ml ampicillin. Plasmid DNAs were prepared using the Wizard miniprep kit (Promega, Madison, Wis.). Inserts were analyzed by digesting the plasmid DNA with EcoRI and separating the restriction endonuclease digestion products on an agarose gel.

Plasmid DNA was prepared for DNA sequencing by ethanol precipitation and resuspending in water to achieve a final DNA concentration of 100 μg/ml. DNA sequence analysis was performed using the ABI PRISM™ dye terminator cycle sequencing ready reaction kit with AmpliTaq DNA polymerase, FS. The initial DNA sequence analysis was performed with M13 forward and reverse primers, subsequently primers based on the rat OB-R sequence were utilized. Following amplification in a Perkin-Elmer 9600, the extension products were purified and analyzed on an ABI PRISM 377 automated sequencer (Perkin Elmer, Norwalk, Conn.). DNA sequence data was analyzed with the Sequencher program. Due to the unknown genotype of the lean Zucker rat for the fa allele, either (+/+ or +/fa) the DNA sequence of multiple subclones of each fragment was analyzed to determine the cDNA sequence of the lean rat OB-R.

EXAMPLE 4

Amplification and DNA Sequence Analysis of Lean and fa/fa With Primers ROBR 10 and 17

Once specific lean rat sequence had been obtained from the ROBR 2–8 PCR fragment, rat specific primers ROBR 10 (5'-CTG CAC TTA ACC TGG CCT ATC-3') and ROBR 17 (5'-GGC CAG AAC TGT AAC AGT GTG-3'), SEQ ID Nos:12 and 19, respectively, were synthesized. Using primers ROBR 10 and 17, PCR products were amplified from rat lean hypothalamus, lean lung, fa/fa hypothalamus and fa/fa kidney cDNAs. The PCR conditions used for this reaction were a PCR reaction mix with a total volume of 50 μl containing 5 ng of template (various rat cDNAs mentioned above), 200 ng of primers, 500 μM dNTPs, 1×Buffer 3 from the Expand kit, 0.25 μl each of Taq Polymerase and Taq Expander. Reactants were assembled in thin walled reaction tubes. The amplification protocol was 1 cycle of 92° C. for 30 sec., followed by 32 cycles at 92° C. for 30 sec., 60° C. for 1 min. and 68° C. for 4 min. using a Perkin Elmer 9600 Thermal Cycler.

EXAMPLE 5
Amplification of the 3' Portion of the Rat OB-R cDNA using Semi-nested PCR The 3' end of both the lean and fa/fa rat OB-receptors was obtained by the PCR with an initial amplification of the rat cDNA using a rat specific 5' primer paired with either a degenerate primer that corresponds to the cytoplasmic domain of the human OB-receptor or the 3' UTR of the human or mouse sequences. This was followed by a second short round of amplification with either one of the original primers paired with a nested primer positioned within the originally amplified fragment, or with two nested primers.

Rat specific primers ROBR 15 (5'-TCA CCT TGC TTT GGA AGC C-3'), ROBR 16 (5'-GAC ATG GTC ACA AGA TGT GGG-3') and ROBR 23 (5'-CCT GGA CAC TGT CAC CTG ATG-3'), SEQ ID NOs:17, 18 and 25, respectively, were paired in different combinations with human degenerate primers located in the cytoplasmic domain of the human OB receptor, HOBR 5 (5'-CAT CAT YTC RTC YTT RTT YTT CCA-3'), HOBR 6 (5'-GTY TGR AAY TGI GGC AT-3') and HOBR 7 (5'-TCR CAC ATY TTR TTY TCC AT-3'), SEQ ID NOs:53–55, respectively, which correspond to amino acids WKNKDEMM, MPQFQT, and MENKMCD, SEQ ID NOs:75–77 respectively. Primers from the 3' ends of the human, HOBR 1R (5'-TCT CTC CCA CCC ACA ACT AT-3'), SEQ ID NO:52 and mouse, MOBR 1R (5'-TGG GTT CAT CTG TAG TGG TC-3'),SEQ ID NO:57 OB receptors were also paired with rat specific primers.

PCR reactions were performed with various combinations of the above primer sets in a total volume of 20 μl containing 5 ng of template (lean and fa/fa hypothalamus cDNAs), 100 ng of primers, 500 μM dNTPs, 1×Buffer 3 from the Expand kit, 0.1 μl each of Taq Polymerase and Taq Expander. Reactants were assembled in thin walled reaction tubes for the Perkin Elmer 9600 Thermal cycler. The amplification protocol was 1 cycle of 92° C. for 30 sec., followed by 32 cycles at 92° C. for 30 sec., 45° C. for 1 min. and 68° C. for 4 min. using a Perkin Elmer 9600 Thermal Cycler.

Products were then purified, removing all nucleotides and primers, using the QIAquick PCR purification kit according to the manufacturer's specified protocols and resuspended in 30 μl of water. The second PCR step was then performed using the first PCR reaction as the template and a nested rat specific primer paired with the original 3' primer as outlined above. The reaction conditions were a 50 μl reaction containing 5 μl of template (from the purified PCR product), 200 ng of primers, 500 μM dNTPs, 1×Buffer 3 from the Expand kit, 0.25 μl each of Taq Polymerase and Taq Expander. Reactants were assembled in thin walled reaction tubes for the Perkin Elmer 9600 Thermal cycler. The amplification protocol was 1 cycle of 92° C. for 30 sec., followed by 25 cycles at 92° C. for 30 sec., 45° C. for 1 min. and 68° C. for 4 min. using a Perkin Elmer 9600 Thermal Cycler.

The largest fragment that was generated using the strategy was a fragment produced from ROBR 16 and HOBR 1R that was approximately 1500 bp in length. The mouse 3' UTR which presumably encodes a smaller isoform generated by alternative splicing, produced a fragment that was about 650 bp long.

EXAMPLE 6
Amplification of 5' End of the Rat OB Receptor

The 5' end of the rat OB receptor was obtained by using semi-nested PCR in a manner analogous to that described above for the 3' end. In this case the rat specific primers are the 3' primers that were combined with primers from the 5' UTRs of the human OB-receptor. The primers utilized were HOBR 1F (5'-CTT ATG CTG GGA TGT GCC-3'), SEQ ID NO:50, and HOBR 1F-2 (5'-TCG TGG CAT TAT CCT TCA G-3') paired with either ROBR 11 (5'-GAT AGG CCA GGT TAA GTG CAG-3'), SEQ ID NO:13, or ROBR 12 (5'-GAG TGC GGA GCA GTT TTG AC-3), SEQ ID NO:14. The largest product, HOBR 1F-2 and ROBR 11, yielded a 500 bp fragment that covers the region and induces an initiator methionine codon.

EXAMPLE 7
Identification of a Nucleotide Change in the fa/fa cDNA

PCR fragments obtained from fa/fa cDNA were prepared for DNA sequence analysis by separating the PCR products on an agarose gel, excising the band of interest, and extracting the DNA using Prep-A-Gene (BioRad). Sequencing results of the PCR product generated from fa/fa hypothalamic cDNA identified a single nucleotide change relative to the lean cDNA sequence. An A to C transversion at bp 880 results in an amino acid change of glutamine to proline at amino acid residue 269. The A to C change in the sequence introduces a MspI restriction endonuclease site (CCGG) into the sequence.

Several independent PCR products were amplified from hypothalamus, lung and kidney cDNA from lean and fa/fa tissues using the primer pair ROBR 10 and 17. This product contains only one endogenous Msp I site at nucleotide 1907. Restriction digestion of the PCR products in a reaction that consisted of 5 μl of the PCR reaction, 4 μl of water and 1 μl of the restriction endonuclease Msp I. These were mixed, incubated for 1 hr at 37° C. and analyzed on a 1% agarose gel. The PCR products from the lean rat cDNAs contained only the endogenous Msp I site and generated products of 1774 and 289 bp. In contrast the PCR products from the fa/fa cDNAs contained an additional Msp I site identified during the sequencing of ROBR 10/17 and generated products of 747, 1027, and 289. Thus, every tissue examined in the fa/fa rat was homozygous for the A to C mutation at nucleotide 880.

EXAMPLE 8
Genotype Analysis of Lean and Fa/fa Rats

Genomic DNA was prepared from a 2 cm portion of the tail from ten lean and ten fa/fa Zucker rats and 2 lean and 5 fa/fa ZDF rats. The tissue was digested overnight at 55° C. using 0.3 μg of Proteinase K in 0.7 ml buffer containing 50 mM Tris, pH 8.0, 100 mM EDTA, and 0.5% SDS. The DNA was extracted two times with phenol/chloroform and one time with chloroform. The DNA was precipitated by adding NaCl to achieve a concentration of 0.3M and then adding an equal volume of 100% ethanol. The DNA was transferred to a 70% wash and then resuspended in 10 mM Tris, 1 mM EDTA.

Genomic DNA, obtained as outlined above from various sources, was diluted in water to a final concentration of approximately 100 ng/ul. In this experiment, the reaction conditions were a 20 μl reaction containing 1 μl of genomic DNA template, 100 ng of primers, 500 μM dNTPs, 1×Buffer 3 from the Expand kit, 0.25 μl each of Taq Polymerase and Taq Expander. Reactants were assembled in Perkin Elmer 0.5 ml thin walled reaction tubes. The amplification protocol for a Perkin Elmer 480 Thermal Cycler was 32 cycles of 92° C. for 30 sec., 54° C. for 1 min. and 68° C. for 5 min. Primers ROBR 27 (5'-GTT TGC GTA TGG AAG TCA CAG-3'), SEQ ID NO:29, and ROBR 28 (5'-ACC AGC AGA GAT GTA TCC GAG-3'), SEQ ID NO:30, were used to amplify a 1.8 Kbp fragment that must contain approximately 1.65 Kbp of intronic sequence since these primers only produce a 156 bp PCR fragment when amplifying cDNA.

After PCR amplification, an Msp I restriction endonuclease digestion of the products was undertaken. The reaction contained 5 μl of the PCR reaction, 4 μl of water and 1 μl of the restriction endonuclease Msp I. These were mixed and incubated for 1 hr at 37° C. The products were then analyzed on a 1% agarose gel. The PCR products contained an endogenous Msp I site that cleaves the fragment somewhere in the intron and produces a 700 bp fragment. Thus, the Msp I restriction endonuclease digestion of the 1800 bp ROBR 27/28 PCR product from a homozygous lean rat yields two fragments of 1100 bp and the endogenous 700 bp fragment. In contrast, Msp I digestion of PCR products from a fa/fa ROBR 27/28 PCR amplification, which contains the A to C mutation, introduces an additional Msp I site that cleaves the 1100 bp band to produce a 950 bp and a small fragment of 130 bp. The genomic analysis of the lean Zucker and ZDF rats also demonstrated that Fa/fa heterozygotes where present as illustrated by Msp I restriction endonuclease digestion patterns that showed that these rats had the 1100 bp fragments as well as the 950 mutant fragment.

What is claimed is:

1. An isolated nucleic acid encoding a rat ob-receptor (OB-R), said receptor comprising the sequence of SEQ ID NO:1.

2. A nucleic acid according to claim 1 which is a DNA.

3. A vector comprising a nucleic acid in accordance with claim 1.

4. A vector according to claim 3 which is a plasmid.

5. A vector according to claim 3 which is a viral vector.

6. A host cell containing a vector according to claim 3.

7. A host cell according to claim 6 which is E. coli, a mammalian cell, or a yeast cell.

8. An isolated nucleic acid in accordance with claim 1 wherein said nucleic acid comprises the sequence of SEQ ID NO:2 from nucleotide 75 to nucleotide 3563.

9. A vector comprising a nucleic acid in accordance with claim 8.

10. A host cell comprising the vector of claim 9.

11. An isolated DNA encoding fa OB-R said DNA comprising the sequence of SEQ ID NO:2 wherein nucleotide 880 is a C instead of an A.

12. A vector comprising a DNA in accordance with claim 11.

13. A host cell comprising the vector of claim 12.

14. An isolated nucleic acid encoding a rat fa ob-receptor (OB-R), said receptor comprising the sequence of SEQ ID NO:1 wherein amino acid 269 is a proline instead of a glutamine.

15. A vector comprising a nucleic acid in accordance with claim 14.

16. A host cell comprising the vector of claim 15.

* * * * *

SEQUENCE LISTING (1) GENERAL INFORMATION:

(iii) NUMBER OF SEQUENCES: 77

(2) INFORMATION FOR SEQ ID NO:1:

(i) SEQUENCE CHARACTERISTICS:
      (A) LENGTH: 1162 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Met Thr Cys Gln Lys Phe Tyr Val Val Leu Leu His Trp Glu Phe Leu
1               5                   10                  15

Tyr Val Ile Thr Ala Leu Asn Leu Ala Tyr Pro Thr Ser Pro Trp Arg
            20                  25                  30

Phe Lys Leu Phe Cys Ala Pro Pro Ser Thr Thr Asp Asp Ser Phe Leu
            35                  40                  45

Ser Pro Ala Gly Val Pro Asn Asn Thr Ser Ser Leu Lys Gly Ala Ser
    50                  55                  60

Glu Ala Leu Val Glu Ala Lys Phe Asn Ser Thr Gly Ile Tyr Val Ser
65                  70                  75                  80

Glu Leu Ser Lys Thr Ile Phe His Cys Cys Phe Gly Asn Glu Gln Gly
                85                  90                  95

Gln Asn Cys Ser Ala Leu Thr Gly Asn Thr Glu Gly Lys Thr Leu Ala
                100                 105                 110

Ser Val Val Lys Pro Leu Val Phe Arg Gln Leu Gly Val Asn Trp Asp
            115                 120                 125

Ile Glu Cys Trp Met Lys Gly Asp Leu Thr Leu Phe Ile Cys His Met
            130                 135                 140

Glu Pro Leu Leu Lys Asn Pro Phe Lys Asn Tyr Asp Ser Lys Val His
145                 150                 155                 160

Leu Leu Tyr Asp Leu Pro Glu Val Ile Asp Asp Leu Pro Leu Pro Pro
                165                 170                 175

Leu Lys Asp Ser Phe Gln Thr Val Gln Cys Asn Cys Ser Val Arg Glu
                180                 185                 190

Cys Glu Cys His Val Pro Val Pro Arg Ala Lys Val Asn Tyr Ala Leu
            195                 200                 205
```

-continued

```
Leu Met Tyr Leu Glu Ile Thr Ser Ala Gly Val Ser Phe Gln Ser Pro
    210                 215                 220
Leu Met Ser Leu Gln Pro Met Leu Val Val Lys Pro Asp Pro Pro Leu
225                 230                 235                 240
Gly Leu Arg Met Glu Val Thr Asp Asp Gly Asn Leu Lys Ile Ser Trp
                245                 250                 255
Asp Ser Gln Thr Lys Ala Pro Phe Pro Leu Gln Tyr Gln Val Lys Tyr
                260                 265                 270
Leu Glu Asn Ser Thr Ile Val Arg Glu Ala Ala Glu Ile Val Ser Asp
                275                 280                 285
Thr Ser Leu Leu Val Asp Ser Val Leu Pro Gly Ser Ser Tyr Glu Val
    290                 295                 300
Gln Val Arg Ser Lys Arg Leu Asp Gly Ser Gly Val Trp Ser Asp Trp
305                 310                 315                 320
Ser Leu Pro Gln Leu Phe Thr Thr Gln Asp Val Met Tyr Phe Pro Pro
                325                 330                 335
Lys Ile Leu Thr Ser Val Gly Ser Asn Ala Ser Phe Cys Cys Ile Tyr
                340                 345                 350
Lys Asn Glu Asn Gln Thr Ile Ser Ser Lys Gln Ile Val Trp Trp Met
                355                 360                 365
Asn Leu Ala Glu Lys Ile Pro Glu Thr Gln Tyr Asn Thr Val Ser Asp
    370                 375                 380
His Ile Ser Lys Val Thr Phe Ser Asn Leu Lys Ala Thr Arg Pro Arg
385                 390                 395                 400
Gly Lys Phe Thr Tyr Asp Ala Val Tyr Cys Cys Asn Glu Gln Ala Cys
                405                 410                 415
His His Arg Tyr Ala Glu Leu Tyr Val Ile Asp Val Asn Ile Asn Ile
                420                 425                 430
Ser Cys Glu Thr Asp Gly Tyr Leu Thr Lys Met Thr Cys Arg Trp Ser
    435                 440                 445
Pro Ser Thr Ile Gln Ser Leu Val Gly Ser Thr Val Gln Leu Arg Tyr
    450                 455                 460
His Arg Arg Ser Leu Tyr Cys Pro Asp Asn Pro Ser Ile Arg Pro Thr
465                 470                 475                 480
Ser Glu Leu Lys Asn Cys Val Leu Gln Thr Asp Gly Phe Tyr Glu Cys
                485                 490                 495
Val Phe Gln Pro Ile Phe Leu Leu Ser Gly Tyr Thr Met Trp Ile Arg
                500                 505                 510
Ile Asn His Ser Leu Gly Ser Leu Asp Ser Pro Pro Thr Cys Val Leu
                515                 520                 525
Pro Asp Ser Val Val Lys Pro Leu Pro Pro Ser Asn Val Lys Ala Glu
    530                 535                 540
Ile Thr Ile Asn Thr Gly Leu Leu Lys Val Ser Trp Glu Lys Pro Val
545                 550                 555                 560
Phe Pro Glu Asn Asn Leu Gln Phe Gln Ile Arg Tyr Gly Leu Asn Gly
                565                 570                 575
Lys Glu Ile Gln Trp Lys Thr His Glu Val Phe Asp Ala Lys Ser Lys
                580                 585                 590
Ser Ala Ser Leu Pro Val Ser Asp Leu Cys Ala Val Tyr Val Val Gln
    595                 600                 605
Val Arg Cys Arg Arg Leu Asp Gly Leu Gly Tyr Trp Ser Asn Trp Ser
610                 615                 620
```

-continued

```
Ser Pro Ala Tyr Thr Leu Val Met Asp Val Lys Val Pro Met Arg Gly
625                 630                 635                 640

Pro Glu Phe Trp Arg Ile Met Asp Gly Asp Ile Thr Lys Lys Glu Arg
            645                 650                 655

Asn Val Thr Leu Leu Trp Lys Pro Leu Met Lys Asn Asp Ser Leu Cys
                660                 665                 670

Ser Val Arg Arg Tyr Val Val Lys His Arg Thr Ala His Asn Gly Thr
            675                 680                 685

Trp Ser Gln Asp Val Gly Asn Gln Thr Asn Leu Thr Phe Leu Trp Ala
    690                 695                 700

Glu Ser Ala His Thr Val Thr Val Leu Ala Ile Asn Ser Ile Gly Ala
705                 710                 715                 720

Ser Leu Val Asn Phe Asn Leu Thr Phe Ser Trp Pro Met Ser Lys Val
                725                 730                 735

Asn Ala Val Gln Ser Leu Ser Ala Tyr Pro Leu Ser Ser Ser Cys Val
                740                 745                 750

Ile Leu Ser Trp Thr Leu Ser Pro Asn Asp Tyr Ser Leu Leu Tyr Leu
            755                 760                 765

Val Ile Glu Trp Lys Asn Leu Asn Asp Asp Gly Met Lys Trp Leu
770                 775                 780

Arg Ile Pro Ser Asn Val Asn Lys Tyr Tyr Ile His Asp Asn Phe Ile
785                 790                 795                 800

Pro Ile Glu Lys Tyr Gln Phe Ser Leu Tyr Pro Val Phe Met Glu Gly
                805                 810                 815

Val Gly Lys Pro Lys Ile Ile Asn Gly Phe Thr Lys Asp Asp Ile Ala
            820                 825                 830

Lys Gln Gln Asn Asp Ala Gly Leu Tyr Val Ile Val Pro Ile Ile Ile
            835                 840                 845

Ser Ser Cys Val Leu Leu Leu Gly Thr Leu Leu Ile Ser His Gln Arg
    850                 855                 860

Met Lys Lys Leu Phe Trp Asp Asp Val Pro Asn Pro Lys Asn Cys Ser
865                 870                 875                 880

Trp Ala Gln Gly Leu Asn Phe Gln Lys Pro Glu Thr Phe Glu His Leu
                885                 890                 895

Phe Thr Lys His Ala Glu Ser Val Ile Phe Gly Pro Leu Leu Leu Glu
                900                 905                 910

Pro Glu Pro Val Ser Glu Glu Ile Ser Val Asp Thr Ala Trp Lys Asn
            915                 920                 925

Lys Asp Glu Met Val Pro Ala Ala Met Val Ser Leu Leu Leu Thr Thr
    930                 935                 940

Pro Asp Ser Thr Arg Gly Ser Ile Cys Ile Ser Asp Gln Cys Asn Ser
945                 950                 955                 960

Ala Asn Phe Ser Gly Ala Gln Ser Thr Gln Gly Thr Cys Glu Asp Glu
                965                 970                 975

Cys Gln Ser Gln Pro Ser Val Lys Tyr Ala Thr Leu Val Ser Asn Val
            980                 985                 990

Lys Thr Val Glu Thr Asp Glu Glu Gln Gly Ala Ile His Ser Ser Val
            995                 1000                1005

Ser Gln Cys Ile Ala Arg Lys His Ser Pro Leu Arg Gln Ser Phe Ser
        1010                1015                1020

Ser Asn Ser Trp Glu Ile Glu Ala Gln Ala Phe Phe Leu Leu Ser Asp
025                 1030                1035                1040

His Pro Pro Asn Val Ile Ser Pro Gln Leu Ser Phe Ser Gly Leu Asp
```

-continued

```
                    1045                1050                1055
Glu Leu Leu Glu Leu Glu Gly Asn Phe Pro Glu Asn His Gly Glu
            1060                1065                1070
Lys Ser Val Tyr Tyr Leu Gly Val Ser Gly Asn Lys Arg Glu Asn
        1075                1080                1085
Asp Met Leu Leu Thr Asp Glu Ala Gly Val Leu Cys Pro Phe Pro Ala
    1090                1095                1100
His Cys Leu Phe Ser Asp Ile Arg Ile Leu Gln Glu Ser Cys Ser His
105                 1110                1115                1120
Phe Val Glu Asn Asn Leu Asn Leu Gly Thr Ser Gly Lys Asn Phe Val
                1125                1130                1135
Pro Tyr Met Pro Gln Phe Gln Ser Cys Ser Thr His Ser His Lys Ile
            1140                1145                1150
Ile Glu Asn Lys Met Cys Asp Leu Thr Val
        1155                1160
```

(2) INFORMATION FOR SEQ ID NO:2:

(i) SEQUENCE CHARACTERISTICS:
        (A) LENGTH: 3650 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
TGGGGCAATT GGGCTGACCT TTCTTATGCT GGGATGTGCC TTGGAGGACT ATGGGTGTCT    60
ATCTCTGAAG TAAGATGACG TGTCAGAAAT TCTATGTGGT TTTGTTACAC TGGGAATTTC   120
TGTATGTGAT AACTGCACTT AACCTGGCCT ATCCAACCTC TCCCTGGAGA TTTAAGCTGT   180
TTTGTGCGCC ACCGAGTACA ACTGATGACT CCTTTCTCTC TCCTGCTGGA GTCCCAAACA   240
ATACTTCGTC TTTGAAGGGG GCTTCTGAAG CACTTGTTGA AGCTAAATTT AATTCAACTG   300
GTATCTACGT TTCTGAGTTA TCCAAAACCA TTTTCCACTG TTGCTTTGGG AATGAGCAAG   360
GTCAAAACTG CTCCGCACTC ACAGGCAACA CTGAAGGGAA GACGCTGGCT TCAGTGGTGA   420
AGCCTTTAGT TTTCCGCCAA CTAGGTGTAA ACTGGGACAT AGAGTGCTGG ATGAAAGGGG   480
ACTTGACATT ATTCATCTGT CATATGGAAC CATTACTTAA GAACCCCTTC AAGAATTATG   540
ACTCTAAGGT TCACCTTTTA TATGATCTGC CTGAAGTTAT AGATGATTTG CCTCTGCCCC   600
CACTGAAAGA CAGCTTTCAG ACTGTCCAGT GCAACTGCAG TGTTCGGGAA TGCGAATGTC   660
ATGTACCAGT ACCCAGAGCC AAAGTCAACT ACGCTCTTCT GATGTATTTA GAAATCACAT   720
CTGCTGGTGT GAGTTTTCAG TCACCTCTAA TGTCACTGCA GCCCATGCTT GTTGTGAAGC   780
CCGATCCACC GCTGGGTTTG CGTATGGAAG TCACAGATGA TGGTAATTTA AAGATTTCAT   840
GGGACAGCCA AACAAAAGCA CCATTTCCAC TTCAATATCA GGTGAAATAT TTAGAGAATT   900
CTACAATCGT AAGAGAGGCT GCTGAAATCG TCTCGGATAC ATCTCTGCTG GTAGACAGCG   960
TGCTTCCTGG GTCTTCATAC GAGGTCCAGG TGAGGAGCAA GAGACTGGAT GGCTCAGGAG  1020
TCTGGAGTGA CTGGAGTTTA CCTCAACTCT TTACCACACA AGATGTCATG TATTTTCCAC  1080
CCAAAATTCT GACGAGTGTT GGATCCAATG CTTCCTTTTG CTGCATCTAC AAAAATGAGA  1140
ACCAGACTAT CTCCTCAAAA CAAATAGTTT GGTGGATGAA TCTAGCCGAG AAGATCCCCG  1200
AGACACAGTA CAACACTGTG AGTGACCACA TTAGCAAAGT CACTTTCTCC AACCTGAAAG  1260
CCACCAGACC TCGAGGGAAG TTTACCTATG ATGCAGTGTA CTGCTGCAAT GAGCAGGCAT  1320
```

-continued

```
GCCATCACCG CTACGCTGAA TTATATGTGA TCGATGTCAA TATCAATATA TCATGTGAAA    1380

CTGACGGGTA CTTAACTAAA ATGACTTGCA GATGGTCACC CAGCACAATC CAATCACTAG    1440

TGGGAAGCAC TGTGCAGTTG AGGTATCACA GGCGCAGCCT GTACTGTCCC GATAATCCAT    1500

CTATTCGTCC TACATCAGAG CTCAAAAACT GCGTCTTACA GACAGATGGC TTTTATGAAT    1560

GTGTTTTCCA GCCAATCTTT CTATTATCTG GCTATACAAT GTGGATCAGG ATCAACCATT    1620

CTTTAGGTTC ACTTGACTCT CCACCAACGT GTGTCCTTCC TGACTCCGTA GTAAAACCAC    1680

TACCTCCATC TAATGTAAAA GCAGAGATTA CTATAAACAC TGGATTATTG AAAGTATCTT    1740

GGGAAAAGCC AGTCTTTCCA GAGAATAACC TTCAGTTCCA GATTCGATAT GGCTTAAATG    1800

GAAAAGAAAT ACAATGGAAG ACACACGAGG TATTCGATGC AAAATCAAAA TCGGCCAGCC    1860

TGCCAGTGTC AGATCTCTGT GCGGTCTATG TGGTACAGGT TCGCTGCCGG CGGTTGGATG    1920

GACTAGGGTA TTGGAGTAAT TGGAGCAGTC CAGCCTACAC TCTTGTCATG GATGTAAAAG    1980

TTCCTATGAG AGGGCCTGAA TTCTGGAGAA TAATGGATGG GGATATTACT AAAAAGGAGA    2040

GAAATGTCAC CTTGCTTTGG AAGCCACTGA TGAAAAATGA CTCACTGTGT AGTGTGAGGA    2100

GGTATGTGGT GAAGCATCGT ACTGCCCACA ATGGGACATG GTCACAAGAT GTGGGAAATC    2160

AGACCAATCT CACTTTCCTG TGGGCAGAAT CAGCACACAC TGTTACAGTT CTGGCCATCA    2220

ATTCCATCGG TGCCTCCCTT GTGAATTTTA ACCTTACGTT CTCATGGCCC ATGAGTAAAG    2280

TGAATGCTGT GCAGTCACTC AGTGCTTATC CCCTGAGCAG CAGCTGCGTC ATCCTTTCCT    2340

GGACACTGTC ACCTAATGAT TATAGTCTGT TATATCTGGT TATTGAATGG AAGAACCTTA    2400

ATGATGATGA TGGAATGAAG TGGCTTAGAA TCCCTTCGAA TGTTAACAAG TATTATATCC    2460

ATGATAATTT TATTCCTATC GAGAAATATC AGTTTAGTCT TTACCCAGTA TTTATGGAAG    2520

GAGTTGGAAA ACCAAAGATA ATTAATGGTT TCACCAAAGA TGATATCGCC AAACAGCAAA    2580

ATGATGCAGG GCTGTATGTC ATTGTACCGA TAATTATTTC CTCTTGTGTC CTGCTGCTCG    2640

GAACACTGTT AATTTCACAC CAGAGAATGA AAAAGTTGTT TTGGGACGAT GTTCCAAACC    2700

CCAAGAATTG TTCCTGGGCA CAAGGACTTA ATTTCCAAAA GCCTGAAACA TTTGAGCATC    2760

TTTTTACCAA GCATGCAGAA TCAGTGATAT TTGGTCCTCT TCTTCTGGAG CCTGAACCAG    2820

TTTCAGAAGA AATCAGTGTC GATACAGCTT GGAAAAATAA AGATGAGATG GTACCAGCAG    2880

CTATGGTCTC ACTTCTTTTG ACCACTCCAG ATTCCACAAG GGGTTCTATT TGTATCAGTG    2940

ACCAGTGTAA CAGTGCTAAC TTCTCTGGGG CTCAGAGCAC CCAGGGAACC TGTGAGGATG    3000

AGTGTCAGAG TCAACCCTCA GTTAAATATG CAACGCTGGT CAGCAACGTG AAAACAGTGG    3060

AAACTGATGA AGAGCAAGGG GCTATACATA GTTCTGTCAG CCAGTGCATC GCCAGGAAAC    3120

ATTCCCCACT GAGACAGTCT TTTTCTAGCA ACTCCTGGGA GATAGAGGCC CAGGCATTTT    3180

TCCTTTTATC AGATCATCCA CCCAATGTGA TTTCACCACA ACTTTCATTC TCAGGGTTGG    3240

ATGAGCTTTT GGAACTGGAG GGAAATTTTC CTGAAGAAAA TCACGGGGAA AAATCTGTGT    3300

ATTATCTAGG AGTCTCCTCA GGAAACAAAA GAGAGAATGA TATGCTTTTG ACTGATGAGG    3360

CAGGGGTATT GTGCCCATTC CCAGCTCACT GTCTGTTCAG TGACATCAGA ATCCTCCAGG    3420

AGAGTTGTTC ACACTTTGTA GAAAATAATT TGAATTTAGG GACCTCTGGT AAGAACTTTG    3480

TACCTTACAT GCCCCAGTTT CAATCCTGTT CCACTCACAG TCATAAGATA ATAGAAAATA    3540

AGATGTGTGA CTTAACTGTG TAATCTTGTC CAAAAACTTC CAGGTTCCAT TCCAGTAGAG    3600

TGTGTCATGT ATAATATGTT CTTTTATAGT TGTGGGTGGG AGAGAAAGCC                3650
```

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ATGATGTGYC ARAARTTYT                                  19

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CAYTGGGART TYCTTTAYGT                                20

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GARTGYTGGA TGAARGG                                    17

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AARCARATTG TTTGGTGG                                  18

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GGTTAYACTA TGTGGAT                                    17

(2) INFORMATION FOR SEQ ID NO:8:

(i) SEQUENCE CHARACTERISTICS:

(A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

ATCCACATTG TRTATCC                                                  17

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CTCCARTTRC TCCARTATCC                                               20

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

ACYTTRCTCA TTGGCCA                                                  17

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CCAYTTCATT CCRTCRTC                                                 18

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CTGCACTTAA CCTGGCCTAT C                                             21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GATAGGCCAG GTTAAGTGCA G                                                     21

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GAGTGCGGAG CAGTTTTGAC                                                       20

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GTCTCGGATA CATCTCTGCT GG                                                    22

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GATTGGATTG TGCTGGGTG                                                        19

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TCACCTTGCT TTGGAAGCC                                                        19

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
GACATGGTCA CAAGATGTGG G                                              21

(2) INFORMATION FOR SEQ ID NO:19:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:19:

GGCCAGAACT GTAACAGTGT G                                              21

(2) INFORMATION FOR SEQ ID NO:20:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:20:

CGCCAACTAG GTGTAAACTG G                                              21

(2) INFORMATION FOR SEQ ID NO:21:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:21:

TGACTTCCAT ACGCAAACCC                                                20

(2) INFORMATION FOR SEQ ID NO:22:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:22:

GAAGCACTGT GCAGTTGAGG                                                20

(2) INFORMATION FOR SEQ ID NO:23:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:23:

GGAAGACACA CGAGGTATTC G                                              21
```

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

CCAGAGCCAA AGTCAACTAC G                                      21

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

CCTGGACACT GTCACCTGAT G                                      21

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

CATYTCRTCY TTRTTYTTCC A                                      21

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

TCRCACATYT TRTTYTTCCA                                        20

(2) INFORMATION FOR SEQ ID NO:28:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

AAYTGTGGCA TRTATCC                                            17

(2) INFORMATION FOR SEQ ID NO:29:

(i) SEQUENCE CHARACTERISTICS:
        (A) LENGTH: 21 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GTTTGCGTAT GGAAGTCACA G                                              21

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

ACCAGCAGAG ATGTATCCGA G                                              21

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

CTGCTGCTCG GAACACTG                                                  18

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

AAGTGAGACC ATAGCTGCTG G                                              21

(2) INFORMATION FOR SEQ ID NO:33:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

CTTCTGAAGC CCGATCCAC                                                 19

(2) INFORMATION FOR SEQ ID NO:34:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

GGGACAAAAT TACACAGTTA ATTCACAC                                28

(2) INFORMATION FOR SEQ ID NO:35:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:35:

AATGACATAC AGCCCTGCAT C                                       21

(2) INFORMATION FOR SEQ ID NO:36:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:36:

TTGGAGGACT ATGGGTGTC                                          19

(2) INFORMATION FOR SEQ ID NO:37:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:37:

GAACAGGATT GAAAGTGGG                                          19

(2) INFORMATION FOR SEQ ID NO:38:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:38:

CTACTGGAAT GGAACCTGG                                          19

(2) INFORMATION FOR SEQ ID NO:39:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:39:

```
GGGAATGCGA ATGTCATGTA C                                              21

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

AGCCATCCAG TCTCTTGCTC                                                20

(2) INFORMATION FOR SEQ ID NO:41:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

CACCCAGCAC AATCCAATC                                                 19

(2) INFORMATION FOR SEQ ID NO:42:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

GCCATATCGA ATCTGGAACT G                                              21

(2) INFORMATION FOR SEQ ID NO:43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

ATGATGATGG AATGAAGTGG C                                              21

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

GATGCACTGG CTGACAGAAC                                                20

(2) INFORMATION FOR SEQ ID NO:45:
```

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

GTTCTGTCAG CCAGTGCATC                                               20

(2) INFORMATION FOR SEQ ID NO:46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

TGACTTTGGC TCTGGGTACT G                                             21

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

TTCTCCAGAA TTCAGGCCCT                                               20

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

GGAGCCTGAA CCAGTTTCAG                                               20

(2) INFORMATION FOR SEQ ID NO:49:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

TTTGACTGAT GAGGCAGGG                                                19

(2) INFORMATION FOR SEQ ID NO:50:

(i) SEQUENCE CHARACTERISTICS:
        (A) LENGTH: 18 base pairs
        (B) TYPE: nucleic acid (C) STRANDEDNESS: single
            (D) TOPOLOGY: linear (ii) MOLECULE TYPE: cDNA (xi) SEQUENCE DESCRIPTION: SEQ ID NO:50:

CTTATGCTGG GATGTGCC                                                           18

(2) INFORMATION FOR SEQ ID NO:51:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:51:

TCGTGGCATT ATCCTTCAG                                                          19

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

TCTCTCCCAC CCACAACTAT                                                         20

(2) INFORMATION FOR SEQ ID NO:53:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

CATCATYTCR TCYTTRTTYT TCCA                                                    24

(2) INFORMATION FOR SEQ ID NO:54:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

GTYTGRAAYT GTGGCAT                                                            17

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

TCRCACATYT TRTTYTCCAT                                           20

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

GTTCTGCAAA TCCAGGTGTA                                           20

(2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

TGGGTTCATC TGTAGTGGTC                                           20

(2) INFORMATION FOR SEQ ID NO:58:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:58:

Ser Val Ile Ile Leu Lys Tyr Asn Ile Gln Tyr Arg Thr Lys Asp Ala
1               5                   10                  15

Ser Thr Trp Ser Gln Ile Pro Pro Glu Asp Thr Ala Ser Thr Arg Ser
            20                  25                  30

Ser Phe Thr Val Gln Asp Leu Lys Pro Phe Thr Glu Tyr Val Phe Arg
        35                  40                  45

Ile Arg Cys Met Lys Glu Asp Gly Lys Gly Tyr Trp Ser Asp Trp Ser
    50                  55                  60

Glu Glu Ala Ser
65

(2) INFORMATION FOR SEQ ID NO:59:

(i) SEQUENCE CHARACTERISTICS:
        (A) LENGTH: 75 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:59:

Asn Leu Lys Ile Ser Trp Asp Ser Gln Thr Lys Ala Pro Phe Pro Leu
1               5                   10                  15

```
Gln Tyr Gln Val Lys Tyr Leu Glu Asn Ser Thr Ile Val Arg Glu Ala
            20                  25                  30

Ala Glu Ile Val Ser Asp Thr Ser Leu Leu Val Asn Ser Val Leu Pro
            35                  40                  45

Gly Ser Ser Tyr Glu Val Gln Val Arg Ser Lys Arg Leu Asp Gly Ser
    50                  55                  60

Gly Val Trp Ser Asp Trp Ser Leu Pro Gln Leu
65                  70                  75
```

(2) INFORMATION FOR SEQ ID NO:60:

(i) SEQUENCE CHARACTERISTICS:
        (A) LENGTH: 75 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:60:

```
Asn Leu Lys Ile Ser Trp Asp Ser Gln Thr Met Ala Pro Phe Pro Leu
1               5                   10                  15

Gln Tyr Gln Val Lys Tyr Leu Glu Asn Ser Thr Ile Val Arg Glu Ala
            20                  25                  30

Ala Glu Ile Val Ser Ala Thr Ser Leu Leu Val Asp Ser Val Leu Pro
            35                  40                  45

Gly Ser Ser Tyr Glu Val Gln Val Arg Ser Lys Arg Leu Asp Gly Ser
    50                  55                  60

Gly Val Trp Ser Asp Trp Ser Ser Pro Gln Val
65                  70                  75
```

(2) INFORMATION FOR SEQ ID NO:61:

(i) SEQUENCE CHARACTERISTICS:
        (A) LENGTH: 76 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:61:

```
Asn Leu Lys Ile Ser Trp Ser Ser Pro Pro Leu Val Pro Phe Pro Leu
1               5                   10                  15

Gln Tyr Gln Val Lys Tyr Ser Glu Asn Ser Thr Thr Val Ile Arg Glu
            20                  25                  30

Ala Asp Lys Ile Val Ser Ala Thr Ser Leu Leu Val Asp Ser Ile Leu
            35                  40                  45

Pro Gly Ser Ser Tyr Glu Val Gln Val Arg Gly Lys Arg Leu Asp Gly
    50                  55                  60

Pro Gly Ile Trp Ser Asp Trp Ser Thr Pro Arg Val
65                  70                  75
```

(2) INFORMATION FOR SEQ ID NO:62:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:62:

Leu Leu Lys Val Ser Trp Glu Lys Pro Val Phe Pro Glu Asn Asn Leu
 1               5                  10                  15

Gln Phe Gln Ile Arg Tyr Gly Leu Asn Gly Lys Glu Ile Gln Trp Lys
                20                  25                  30

Thr His Glu Val Phe Asp Ala Lys Ser Lys Ser Ala Ser Leu Pro Val
                35                  40                  45

Ser Asp Leu Cys Ala Val Tyr Val Val Gln Val Arg Cys Arg Arg Leu
     50                  55                  60

Asp Gly Leu Gly Tyr Trp Ser Asn Trp Ser Ser Pro Ala
 65                  70                  75

(2) INFORMATION FOR SEQ ID NO:63:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:63:

Leu Leu Lys Val Ser Trp Glu Lys Pro Val Phe Pro Glu Asn Asn Leu
 1               5                  10                  15

Gln Phe Gln Ile Arg Tyr Gly Leu Ser Gly Lys Glu Ile Gln Trp Lys
                20                  25                  30

Thr His Glu Val Phe Asp Ala Lys Ser Lys Ser Ala Ser Leu Leu Val
                35                  40                  45

Ser Asp Leu Cys Ala Val Tyr Val Val Gln Val Arg Cys Arg Arg Leu
     50                  55                  60

Asp Gly Leu Gly Tyr Trp Ser Asn Trp Ser Ser Pro Ala
 65                  70                  75

(2) INFORMATION FOR SEQ ID NO:64:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:64:

Leu Leu Lys Ile Ser Trp Glu Lys Pro Val Phe Pro Glu Asn Asn Leu
 1               5                  10                  15

Gln Phe Gln Ile Arg Tyr Gly Leu Ser Gly Lys Glu Val Gln Trp Lys
                20                  25                  30

Met Tyr Glu Val Tyr Asp Ala Lys Ser Lys Ser Val Ser Leu Pro Val
                35                  40                  45

Pro Asp Leu Cys Ala Val Tyr Ala Val Gln Val Arg Cys Lys Arg Leu
     50                  55                  60

Asp Gly Leu Gly Tyr Trp Ser Asn Trp Ser Asn Pro Ala
 65                  70                  75

(2) INFORMATION FOR SEQ ID NO:65:

(i) SEQUENCE CHARACTERISTICS:
        (A) LENGTH: 40 amino acids
        (B) TYPE: amino acid (C) STRANDEDNESS: single
            (D) TOPOLOGY: linear (ii) MOLECULE TYPE: peptide (xi) SEQUENCE DESCRIPTION: SEQ ID NO:65:

Leu Lys Ile Ser Trp Ser Pro Asn Leu Gln Tyr Gln Lys Tyr Asn Val
 1               5                  10                  15

Glu Ala Ser Val Pro Tyr Val Gln Val Arg Cys Lys Arg Leu Asp Gly
                20                  25                  30

Gly Tyr Trp Ser Asp Trp Ser Pro
            35                  40

(2) INFORMATION FOR SEQ ID NO:66:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:66:

Gly Xaa Trp Ser Xaa Trp Ser
 1               5

(2) INFORMATION FOR SEQ ID NO:67:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:67:

Trp Ser Xaa Trp Ser
 1               5

(2) INFORMATION FOR SEQ ID NO:68:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:68:

AGAGCGGACA CTCTTTGAAT ATCT                                           24

(2) INFORMATION FOR SEQ ID NO:69:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:69:

Arg Ala Asp Thr Leu
 1               5

(2) INFORMATION FOR SEQ ID NO:70:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:70:

His Trp Glu Phe Leu Tyr Val
1               5

(2) INFORMATION FOR SEQ ID NO:71:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:71:

Glu Cys Trp Met Lys Gly
1               5

(2) INFORMATION FOR SEQ ID NO:72:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:72:

Gly Tyr Thr Met Trp Ile
1               5

(2) INFORMATION FOR SEQ ID NO:73:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:73:

Val Tyr Trp Ser Asn Trp Ser
1               5

(2) INFORMATION FOR SEQ ID NO:74:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:74:

Trp Pro Met Ser Lys Val
1               5

(2) INFORMATION FOR SEQ ID NO:75:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:75:

Trp Lys Asn Lys Asp Glu Met Met
1               5

(2) INFORMATION FOR SEQ ID NO:76:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:76:

Met Pro Gln Phe Gln Thr
1               5

(2) INFORMATION FOR SEQ ID NO:77:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:77:

Met Glu Asn Lys Met Cys Asp
1               5